United States Patent [19]

Murayama

[11] Patent Number: 5,330,983
[45] Date of Patent: Jul. 19, 1994

[54] 14-O-P-CHLOROBENZOYLACONINE AND ANALGESIC/ANTI-INFLAMMATORY AGENT CONTAINING THE SAME

[75] Inventor: Mitsuo Murayama, Utsunomiya, Japan

[73] Assignee: Sanwa Shoyaku Kabushiki Kaisha, Tochigi, Japan

[21] Appl. No.: 989,018

[22] PCT Filed: Sep. 27, 1991

[86] PCT No.: PCT/JP91/01298
§ 371 Date: Mar. 5, 1993
§ 102(e) Date: Mar. 5, 1993

[30] Foreign Application Priority Data

Jul. 8, 1991 [JP] Japan ................................. 3-263354

[51] Int. Cl.$^5$ ................. C07D 221/22; C07D 223/14; A61K 31/435
[52] U.S. Cl. ..................................... 514/216; 540/581
[58] Field of Search .................... 540/581; 514/216

[56] References Cited

FOREIGN PATENT DOCUMENTS

| | | | |
|---|---|---|---|
| 56-120620 | 9/1981 | Japan | 540/581 |
| 63-211268 | 9/1988 | Japan | 540/581 |
| 63-211269 | 9/1988 | Japan | 540/581 |
| 63-275583 | 11/1988 | Japan | 540/581 |
| 64-34965 | 2/1989 | Japan | 540/581 |
| 1-254625 | 10/1989 | Japan | 540/581 |
| 3-223255 | 10/1991 | Japan | 540/581 |

*Primary Examiner*—Alan L. Rotman
*Attorney, Agent, or Firm*—Nixon & Vanderhye

[57] ABSTRACT

Analgesic/anti-inflammatory agent containing as active ingredient 14-O-p-chlorobenzoylaconine or a salt thereof. 14-O-p-chlorobenzoylaconine is a novel substance and a compound with high safety which shows an analgesic action on both inflammatory and non-inflammatory pains as well as an anti-inflammatory action. This compound can be used in the treatment of pain-causing diseases, both inflammatory and non-inflammatory, as well as in the treatment of inflammation.

2 Claims, No Drawings

14-O-P-CHLOROBENZOYLACONINE AND ANALGESIC/ANTI-INFLAMMATORY AGENT CONTAINING THE SAME

TECHNICAL FIELD

This invention relates to novel compound 14-O-p-chlorobenzoylaconine or a salt thereof, as well as to a novel analgesic/anti-inflammatory agent containing the 14-O-p-chlorobenzoylaconine or salt thereof as active ingredient.

BACKGROUND ART

Aconitine alkaloids contained in the tuberous root of plants of the genus Aconitium have already been reported to have a potent analgesic and anti-inflammatory activity. They, however, are supposed to show a narrow safety margin because of their high toxicity.

DISCLOSURE OF INVENTION

As a result of extensive studies in an attempt to develop novel aconitine alkaloid derivatives which are low in toxicity but maintain the analgesic/anti-inflammatory activity that aconitine alkaloids have, we have already succeeded in providing "novel aconitine compounds and analgesic/anti-inflammatory agent comprising the same" (Japanese patent application No. 2-283553). As a result of further studies, we have now succeeded in providing 14-O-p-chlorobenzoylaconine, a compound with excellent pharmacological effects coupled with high safety.

Thus, the present invention provides a new compound, 14-O-p-chlorobenzoylaconine of the formula:

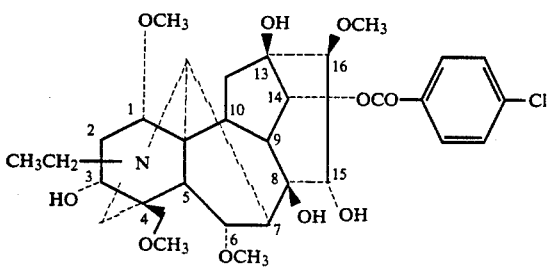

as well as a salt thereof. It also provides an analgesic-/anti-inflammatory agent containing 14-O-p-chlorobenzoylaconine or a salt thereof as active ingredient together with an excipient.

The present invention will now be described in detail in the following.

The compound according to the invention of the formula (I) shown above may be prepared by using as starting material aconitine compounds described in the literature, such as aconitine, mesaconitine, jesaconitine, 14-O-benzoylaconine, 14-O-benzoylmesaconine and 14-O-anisoylaconine shown below by the formulas (II), (III), (IV), (V), (VI) and (VII), respectively.

Where the compounds of the formulas (II), (IV), (V) and (VII) are used as starting material, the compound of the formula (I) may be prepared by deesterification into hydroxyl group of the substituent present at the position 14 or 8 in the form of ester bond, through hydrolysis such as alkaline hydrolysis, followed by reaction with p-chlorobenzoyl chloride in an appropriate solvent such as pyridine.

Where the compounds of the formulas (III) and (VI) are used as starting material, the compound of the formula (I) may be prepared by following the same steps as in the case where the compounds of the formulas (II), (IV), (V) and (VII) are used as starting material, i.e. deesterification into hydroxyl group of the substituent present at the position 14 or 8 in the form of ester bond, through hydrolysis such as alkaline hydrolysis, followed by reaction with p-chlorobenzoyl chloride in an appropriate solvent such as pyridine, to give 14-O-p-chlorobenzoylmesaconine; reacting the product with an appropriate oxidizing agent such as potassium permanganate in an appropriate solvent such as acetone to give N-demethylated product; and reacting the N-demethylated product with an ethylating agent such as ethyl iodide.

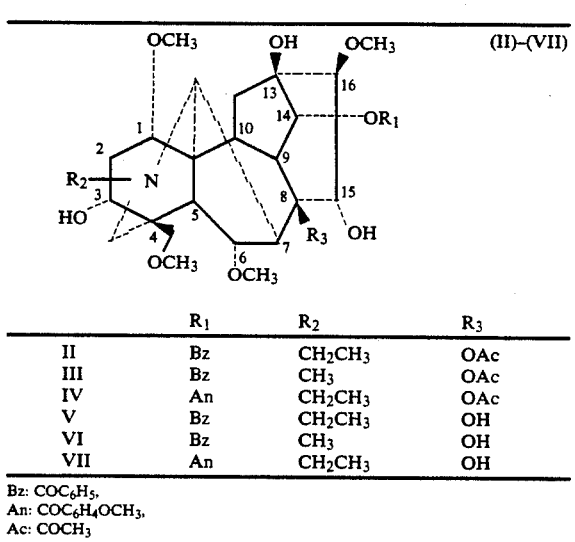

| | $R_1$ | $R_2$ | $R_3$ |
|---|---|---|---|
| II | Bz | $CH_2CH_3$ | OAc |
| III | Bz | $CH_3$ | OAc |
| IV | An | $CH_2CH_3$ | OAc |
| V | Bz | $CH_2CH_3$ | OH |
| VI | Bz | $CH_3$ | OH |
| VII | An | $CH_2CH_3$ | OH |

Bz: $COC_6H_5$,
An: $COC_6H_4OCH_3$,
Ac: $COCH_3$

The compound of the invention is a basic substance capable of forming salts with inorganic acids such as hydrochloric acid, sulfuric acid and hydrobromic acid or with organic acids such as oxalic acid, succinic acid, tartaric acid, citric acid and ascorbic acid.

In the following will now be given working examples and experiment examples regarding the compound of the invention for further illustration of the present invention Physicochemical parameters and analytical data of the compound of the formula (I) prepared in these working examples are given just after the description of the working examples. Pharmacological activity, toxicity etc. of compounds are shown in Tables 1–6 mentioned below.

EXAMPLE 1

100 mg of aconitine was dissolved in 5 ml of 5% KOH in methanol. This solution was stirred at room temperature for 10 hours. The solvent was evaporated off under reduced pressure and the resulting residue was dissolved in 5 ml of ice water. This solution was chromatographed on Amberlite XAD2 (20 ml, product of Nippon Organo) which had been washed with methanol and water in that order. After this column was washed by water until the washings were free from alkalinity, it was eluted with methanol (300 ml). The eluate was dried under reduced pressure to afford 96 mg of residue containing aconine. This residue was dissolved in 2 ml of distilled pyridine. To this solution, 0.06 ml of p-chlorobenzoyl chloride was added and the mixture was stirred at −18° C. for 10 minutes. After reaction, the reaction mixture was chromatographed on a silica gel (10 g) column, eluting with $CHCl_3$ (30 ml), 10% methanol in $CHCl_3$ (30 ml), 15% methanol in $CHCl_3$ and 20% methanol in $CHCl_3$ in that order. The eluates with 10% methanol in $CHCl_3$ and 15% methanol in $CHCl_3$ were mixed and dried under reduced pressure. The residue was subjected to column chromatography on silica gel (30 g), eluting with ammonia-saturated chloroform and the so purified residue was recrystallized from acetone-hexane to afford 14-O-p-chlorobenzoylaconine (83 mg).

EXAMPLE 2

77 mg of 14-O-p-chlorobenzoylaconine was obtained in the same manner as in Example 1, except for the use of 100 mg of jesaconitine as a substitute for aconitine in Example 1.

EXAMPLE 3

85 mg of 14-O-p-chlorobenzoylaconine was obtained in the same manner as in Example 1, except for the use of 100 mg of 14-O-benzoylaconine as a substitute for aconitine in Example 1.

EXAMPLE 4

84 mg of 14-O-p-chlorobenzoylaconine was obtained in the same manner as in Example 1, except for the use of 100 mg of 14-O-anisoylaconine as a substitute for aconitine in Example 1.

EXAMPLE 5

80 mg of 14-O-p-chlorobenzoylmesaconine was obtained in the same manner as in Example 1, except for the use of 100 mg of mesaconitine as a substitute for aconitine in Example 1. 80 mg of 14-O-p-chlorobenzoylmesaconine were dissolved in 10 ml of acetone. To this solution, 4 ml of aqueous $KMnO_4$ solution (887 mg in 25 ml of water) and 0.7 ml of aqueous $K_2CO_3$ solution (556 mg in 4.5 ml of water) were added and the mixture was stirred at room temperature for 30 minutes. The reaction mixture was concentrated under reduced pressure until the odor of acetone was no longer apparent. To the residual solution, 5 ml of 2N $H_2SO_4$ and 3.5 ml of aqueous $Na_2S_2O_3$ solution (887 mg in 22 ml of water) were added and the mixture was washed with $CH_2Cl_2$. The aqueous layer was adjusted to pH 8-9 with $Na_2CO_3$. This solution was extracted with $CH_2Cl_2$. The $CH_2Cl_2$ layer was dried over $Na_2SO_4$ and concentrated to dryness in vacuo. The residue was subjected to column chromatography on silica gel, eluting with 5% methanol in ammonia-saturated $CHCl_3$ to afford de-N-methyl-14-O-p-chlorobenzoylmesaconine (58 mg). 58 mg of de-N-methyl-14-O-p-chlorobenzoylmesaconine was dissolved in 2 ml of a mixture of methanol and ether (1:1). To this solution, 65 mg of $CaCO_3$ and 0.5 ml of $CH_3CH_2I$ were added and the mixture was refluxed for 2 hours. The reaction mixture was filtered off to remove insolubles and concentrated to dryness under reduced pressure. The residue was subjected to column chromatography on silica gel for separation and purification, eluting with 5% methanol in ammonia-saturated $CHCl_3$ to afford 14-O-p-chlorobenzoylaconine (33 mg).

EXAMPLE 6

35 mg of 14-O-p-chlorobenzoylaconine was obtained in the same manner as in Example 5, except for the use of 14-O-benzoylmesaconine as a substitute for mesaconitine in Example 5.

EXAMPLE 7

10 mg of 14-O-p-chlorobenzoylaconine was dissolved in 0.5 ml of ethanol. To this solution, 0.5 ml of an ethanolic solution of L(+)-tartaric acid (23 mg in 5 ml of ethanol) was added and the mixture was well mixed. Then, $N_2$ gas was blowed against this solution to evaporate off the ethanol in the solution to dryness. The residue was placed in a desiccator under reduced pressure to afford the tartaric acid salt of 14-O-p-chlorobenzoylaconine (11.4 mg).

EXAMPLE 8

12.9 mg of the citric acid salt of 14-O-p-chlorobenzoylaconine was obtained in the same manner as in Example 7, except for the use of 32 mg of citric acid as a substitute for L(+)-tartaric acid in Example 7.

EXAMPLE 9

12 mg of the L(+)-ascorbic acid salt of 14-O-p-chlorobenzoylaconine was obtained in the same manner as in Example 7, except for the use of 26 mg of L(+)-ascorbic acid as a substitute for L(+)-tartaric acid in Example 7.

EXAMPLE 10

10.8 mg of the hydrobromic acid salt of 14-O-p-chlorobenzoylaconine was obtained in the same manner as in Example 7, except for the use of 27 mg of hydrobromic acid as a substitute for L(+)-tartaric acid in Example 7.

Physicochemical parameters and analytical data of 14-O-p-chlorobenzoylaconine

1) Analysis of IR spectra (KBr) $IR\nu_{max}^{KBr}$: 3500, 1720 $cm^{-1}$.

2) Analysis of UV spectra (ethanol) UV $\lambda_{max}^{EtOH}$ (log $\epsilon$) nm: 240 (3.98).

3) Analysis of $^1H$—NMR spectra ($CDCl_3$) The following signals are shown ($\delta$, ppm). 7.99 and 7.40 (each 2H, d, J=8.9 Hz, p-chlorobenzoyl group), 4.97 (1H, d, J=5.4 Hz, C14-H), 3.71, 3.31, 3.30 and 3.26 (each 3H, s, $OCH_3$ at C1, C6, C16 and C18), 1.10 (3H, t, J=7.0 Hz, $CH_3$ of $C_2H_5$ at the nitrogen atom).

4) Analysis of $^{13}C$—NMR spectra ($CDCl_3$) The following signals are shown ($\delta$, ppm). 165.3 (carbonyl of p-chlorobenzoyl group at C14), 139.6, 131.1, 128.8 and 128.2 (p-chlorobenzoyl group), 90.7, 83.0, 82.4, 81.8, 79.9, 78.5, 77.1, 74.6 and 71.6 (C16, C6, C1, C15, C14, C8, C18, C13 and C3), 60.8, 59.1, 58.0 and 55.7 ($OCH_3$ at C16, C18, C6 and C1), 48.9 ($C_2$ of $C_2H_5$ at the nitrogen atom), 13.0 ($CH_3$ of $C_2H_5$ at the nitrogen atom).

5) Analysis of Mass spectra m/z: 637, 639 (M+).

6) Property and solubility Colorless and odorless needles. m.p. 221°-222° C. Soluble in ether, chloroform, benzene, methanol, ethanol, acetone, ethyl acetate, pyridine and dimethyl sulfoxide. Insoluble in hexane and water.

Examples of experiment with respect to the pharmacological property and acute toxicity of the compound shown in formula (I) mentioned above are described below.

EXPERIMENT EXAMPLE 1

Measurement of Analgesic Activity by the Acetic Acid-Induced Writhing Method

Male mice of the Std:ddY Strain (20-25 g), which were fasted for one night before the initiation of the experiment, were used. Test compound hardly soluble in water was used in 3% suspension in gum arabic. Test compound taking a salt form was used in aqueous solution. 0.7% acetic acid in 0.9% physiological saline solution was injected i.p. (10 ml/kg) at 2 hours and 50 minutes after the test compound was administered p.o. After 10 minutes, the number of writhing movements was counted for a period of 10 minutes. The results are shown in Table 1. It was demonstrated in Table 1 that the compounds of this invention had a dose-dependent potent analgesic activity.

EXPERIMENT EXAMPLE 2

Measurement of Analgesic Activity by the Phenylquinone-Induced Writhing Method Male mice of the Std:ddY Strain (20–25 g), which were fasted for one night before the initiation of the experiment, were used. Test compound hardly soluble in water was used in 3% suspension in gum arabic. Test compound taking a salt form was used in aqueous solution. 0.03% phenylquinone in 0.5% ethanol solution was injected i.p. (10 ml/kg) at 2 hours and 55 minutes after the compound was administered p.o. After 5 minutes, the number of writhings was counted for a period of 15 minutes. The results are shown in Table 2 described below. It was demonstrated in Table 2 that the compounds of this invention had a dose-dependent, potent analgesic activity.

EXPERIMENT EXAMPLE 3

Measurement of Analgesic Activity by the Tail-Pressure Method

Male mice of the Std:ddY Strain (20–25 g), which were fasted for one night before the initiation of the experiment, were used. Test compound hardly soluble in water was used in 3% suspension in gum arabic. Test compound taking a salt form was used in aqueous solution. Experiments were made with a tail-pressure apparatus. Before the administration of test compounds, the pain threshold was measured twice at intervals of 30 minutes and those mice indicating a pain threshold of 30 to 80 mmHg were selected and used. The pain threshold of each mouse was measured at 1, 3 and 5 hours after test compounds were administered p.o. The results were described as a percentage of the pain threshold after the treatment with test compound relative to that before the treatment with test compound. The results are shown in Table 3. It was demonstrated in Table 3 that the compounds of this invention had a dose-dependent, potent analgesic activity.

EXPERIMENT EXAMPLE 4

Measurement of Analgesic Activity by the Hot Plate Method

Male mice of the Std:ddY Strain (20–25 g), which were fasted for one night before the initiation of the experiment, were used. Test compound hardly soluble in water was used in 3% suspension in gum arabic. Test compound taking a salt form was used in aqueous solution. Mice were placed on a cyrindric hot plate (diameter: 22 cm, height: 11 cm) made of copper which was fixed in a water bath adjusted to 52° C. so that each animal's four paws came into contact with the plate and the time taken to show the nociceptive response (jumping and licking) as an index of pain was measured. Mice showing response times above 25 seconds were excluded from the experiment. The analgesic activity of the compound was measured at 1, 3 and 5 hours after test compound was administered p.o. The results are shown in Table 4. It was demonstrated in Table 4 that the compound of this invention had a dose-dependent, potent analgesic activity.

EXPERIMENT EXAMPLE 5

Measurement of Antiinflammatory Activity by the Carrageenin-Induced Hind Paw Edema Male rats of the Wistar strain (5 weeks old, 120–130 g), which were fasted for one night before the initiation of the experiment, were used. One hour after the oral administration of test compound, λ-carrageenin (1%) was injected s.c. under the plantar surface of the right hind paw. Thereafter, at one hour intervals for 6 hours, the volume of the paw was measured using an apparatus therefor. The results were described as a swelling rate (%) calculated using the following equation:

$$(R-L) \times 100/L = \text{swelling rate (\%)}$$

R: the volume of the right hind paw
L: the volume of the left hind paw
The results are shown in Table 5. It was demonstrated in Table 5 that the compound of this invention had an inhibitory action against the carrageenin-induced paw edema.

EXPERIMENT EXAMPLE 6 (ACUTE TOXICITY)

Male mice of the Std:ddY Strain (20–25 g), which were fasted for one night before the initiation of the experiment, were used. Test compound hardly soluble in water was used in 3% suspension in gum arabic. Test compound taking a salt form was used in aqueous solution. The $LD_{50}$ values were calculated using the method of Litchfield-Wilcoxon from the mortality during 72 hours after test compound was administered p.o. The results are shown in Table 6. As shown in Table 6, no death of mice was seen even at the p.o. administration of 1000 mg/kg of the compound of this invention and the compound of this invention was thus found to be very low in toxicity.

TABLE 1

Measurement of analgesic activity by the acetic acid-induced writhing method

| Test compound | Dose (mg/kg) | The number of writhings mean ± S.E. |
|---|---|---|
| control | 0 | 31.3 ± 3.5 |
| 8-deoxy-14-O-benzoylaconine | 3 | 24.1 ± 2.7 |
|  | 10 | 21.9 ± 2.6* |
|  | 30 | 17.8 ± 2.5** |
| 14-O-p-chlorobenzoylaconine | 3 | 19.8 ± 2.5* |
|  | 10 | 17.3 ± 2.4** |
|  | 30 | 12.9 ± 3.7** |
| 14-O-p-chlorobenzoylaconine tartrate | 3 | 17.8 ± 2.5** |
|  | 10 | 15.5 ± 2.3** |
|  | 30 | 10.7 ± 2.1** |

*$P < 0.05$,
**$P < 0.01$. n = 10.

TABLE 2

Measurement of analgesic activity by the phenylquinone-induced writhing method

| Test compound | Dose (mg/kg) | The number of writhings mean ± S.E. |
|---|---|---|
| control | 0 | 31.3 ± 3.2 |
| 8-deoxy-14-O-benzoylaconine | 3 | 27.1 ± 2.7 |
|  | 10 | 25.0 ± 3.0 |
|  | 30 | 24.0 ± 2.3* |

TABLE 2-continued

Measurement of analgesic activity by the phenylquinone-induced writhing method

| Test compound | Dose (mg/kg) | The number of writhings mean ± S.E. |
|---|---|---|
| 14-O-p-chlorobenzoylaconine | 3 | 20.1 ± 3.6* |
|  | 10 | 17.3 ± 2.8** |
|  | 30 | 15.9 ± 3.5** |
| 14-O-p-chlorobenzoylaconine tartrate | 3 | 21.1 ± 2.4** |
|  | 10 | 18.3 ± 2.2** |
|  | 30 | 15.7 ± 2.7** |

*$P < 0.05$,
**$P < 0.01$. $n = 8 \sim 10$.

TABLE 3

Measurement of analgesic activity by the tail-pressure method

| Test compound | Dose (mg/kg) | Pain threshold (%, mean ± S.E.)[1] 1 | 3 | 5 (h) |
|---|---|---|---|---|
| control | 0 | 90.7 ± 2.9 | 95.2 ± 2.9 | 92.2 ± 2.8 |
| 8-deoxy-14-O-benzoylaconine | 100 | 101.8 ± 14.1 | 100.2 ± 7.2 | 105.6 ± 9.2 |
|  | 300 | 115.6 ± 17.0* | 116.2 ± 12.0* | 110.2 ± 7.0* |
| 14-O-p-chlorobenzoylaconine | 100 | 100.4 ± 2.5 | 129.6 ± 10.3** | 108.0 ± 6.0* |
|  | 300 | 120.0 ± 7.3** | 182.0 ± 21.7** | 166.0 ± 20.1** |
| 14-O-p-chlorobenzoylaconine tartrate | 100 | 102.6 ± 3.4* | 141.1 ± 8.3** | 128.0 ± 4.9** |
|  | 300 | 147.0 ± 7.8** | 240.4 ± 25.0** | 202.9 ± 19.7** |

*$P < 0.05$,
**$P < 0.01$. $n = 6 \sim 34$.
[1] Percentage of the post-treatment relative to the pre-treatment pain threshold.

TABLE 4

Measurement of analgesic activity by the hot plate method

| Test compound | Dose (mg/kg) | Pain threshold (s, mean ± S.E.) 1 | 3 | 5 (h) |
|---|---|---|---|---|
| control | 0 | 14.3 ± 0.8 | 16.6 ± 0.9 | 18.9 ± 1.4 |
| 8-deoxy-14-O-benzoylaconine | 100 | 17.3 ± 1.7 | 17.9 ± 2.1 | 18.9 ± 1.7 |
|  | 300 | 18.6 ± 1.6* | 24.0 ± 2.3** | 19.6 ± 2.0 |
| 14-O-p-chlorobenzoylaconine | 100 | 21.6 ± 2.2** | 21.6 ± 2.0* | 27.6 ± 0.9** |
|  | 300 | 22.2 ± 1.5** | 38.4 ± 3.3** | 24.0 ± 1.6* |
| 14-O-p-chlorobenzoylaconine tartrate | 100 | 17.3 ± 2.2* | 26.7 ± 3.2** | 24.7 ± 2.1* |
|  | 300 | 18.7 ± 1.7* | 42.5 ± 11.0** | 25.7 ± 2.7* |

*$P < 0.05$,
**$P < 0.01$. $n = 7 \sim 14$.

TABLE 5

Measurement of the carrageenin-induced paw edema (antiinflammatory activity)

| Test compound | Dose (mg/kg) | Swelling rate (%, mean ± S.E.) 1 | 2 | 3 | 4 | 5 | 6 (h) |
|---|---|---|---|---|---|---|---|
| control | 0 | 28.6 ± 5.4 | 38.9 ± 3.3 | 73.5 ± 7.6 | 75.9 ± 4.6 | 80.0 ± 2.1 | 81.2 ± 6.7 |
| 8-deoxy-14-O-benzoylaconine | 100 | 24.8 ± 9.2 | 36.3 ± 6.3 | 59.8 ± 6.3 | 63.5 ± 1.0* | 70.3 ± 3.9* | 72.2 ± 6.0 |
| 14-O-p-chlorobenzoylaconine | 100 | 22.4 ± 8.0 | 28.0 ± 2.4* | 51.0 ± 2.8* | 58.6 ± 2.4* | 66.8 ± 3.7** | 72.9 ± 5.3 |
| 14-O-p-chlorobenzoylaconine tartrate | 100 | 16.0 ± 3.6 | 31.5 ± 3.1 | 47.3 ± 7.4* | 56.1 ± 2.0** | 49.6 ± 5.0** | 57.6 ± 9.0* |

*$P < 0.05$,
**$P < 0.01$. $n = 6 \sim 8$.

TABLE 6

| Toxicity Test compound | $LD_{50}$ (mg/kg) |
|---|---|
| 8-deoxy-14-O-benzoylaconine | 100< |
| 14-O-p-chlorobenzoylaconine | 1000< |
| 14-O-p-chlorobenzoylaconine tartrate | 1000< |

The aforementioned demonstrates that the compound of the formula (I) has an analgesic/anti-inflammatory activity as well as a low toxicity with the $LD_{50}$ being not lower than 1,000 mg/kg.

The dose of the compound of the formula (I) for clinical use as analgesic/anti-inflammatory agent according to the invention is preferably 1–1,000 mg/day for adults. The agent according to the present invention is presented for actual application after formed into desired dosage forms by conventional methods using customarily used carriers or excipients. Wherever appropriate or necessary, the compound of the present invention may be used in the form of a salt thereof for achieving its pharmaceutical effect or facilitating the preparation of dosage forms.

Oral preparations such as tablets, powders, granules and capsules may contain conventional excipients such as calcium carbonate, magnesium carbonate, calcium phosphate, corn starch, potato starch, sugar, lactose, talc, magnesium stearate and gum arabic. Tablets may be coated by conventional methods. Oral liquid preparations may be aqueous or oily suspensions, solutions, syrups, elixirs etc.

For injectable preparations, the compound of the formula (I) may be used in the form of a salt thereof, and preferably reconstituted upon use. Such preparations may contain different adjuvants such as suspending, stabilizing or dispersing agents. They may contain sterilized distilled water, refined oils such as peanut oil and corn oil, non-aqueous solvents, polyethylene glycol, polypropylene glycol, etc.

Preparations for rectal administration are presented in the form of compositions for suppository and may contain pharmaceutical carriers well known in the art such as polyethylene glycol, lanolin and coconut oil.

Preparations for topical application are presented in the form of compositions for ointment, plaster or poultice and may contain pharmaceutical carriers well known in the art such as vaseline, paraffin, hydrous lanolin, plastibase, kaolin, bentonite, talc, aluminum silicate, propylene glycol, sorbitol, hydrophilic petrolatum, macrogols, wax, resin, purified lanolin, gum, glycerin, gelatin, polyacrylic acid, polyacrylic acid salt, polyvinyl alcohol, polyvinyl pyrrolidone and polyethylene oxide.

I claim:

1. 14-O-p-chlorobenzoylaconine of the formula (I)

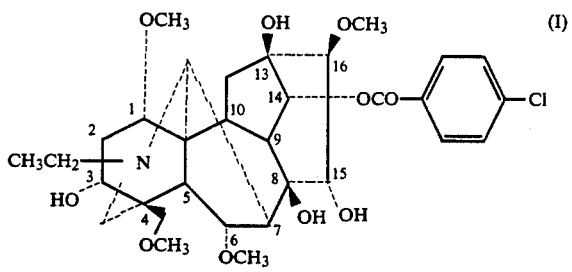

or a pharmaceutically acceptable salt thereof.

2. An analgesic/anti-inflammatory composition comprising as the active ingredient an effective amount of 14-o-p-chlorobenzoylaconine or a pharmaceutically acceptable salt thereof together with a pharmaceutically acceptable excipient or adjuvant.

* * * * *